(12) United States Patent
Merkel et al.

(10) Patent No.: US 9,260,365 B2
(45) Date of Patent: Feb. 16, 2016

(54) PROCESS FOR PRODUCING 2,3,3,3-TETRAFLUOROPROPENE

(71) Applicant: HONEYWELL INTERNATIONAL INC., Morristown, NJ (US)

(72) Inventors: Daniel C. Merkel, Orchard Park, NY (US); Konstantin A. Pokrovski, Orchard Park, NY (US); Hsueh S. Tung, Getzville, NY (US); Haiyou Wang, Amherst, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 14/643,607

(22) Filed: Mar. 10, 2015

(65) Prior Publication Data
US 2015/0183697 A1  Jul. 2, 2015

Related U.S. Application Data

(60) Division of application No. 13/281,063, filed on Oct. 25, 2011, now Pat. No. 8,975,454, and a continuation-in-part of application No. 12/510,740, filed on Jul. 28, 2009, now Pat. No. 8,766,020.

(60) Provisional application No. 61/414,074, filed on Nov. 16, 2010, provisional application No. 61/085,141, filed on Jul. 31, 2008.

(51) Int. Cl.
| | |
|---|---|
| *C07C 17/00* | (2006.01) |
| *C07C 17/38* | (2006.01) |
| *C07C 17/395* | (2006.01) |
| *B01J 27/10* | (2006.01) |
| *C07C 17/25* | (2006.01) |
| *C07C 17/383* | (2006.01) |
| *B01D 3/00* | (2006.01) |
| *B01D 3/10* | (2006.01) |
| *B01D 11/04* | (2006.01) |
| *B01J 19/12* | (2006.01) |
| *C07C 21/18* | (2006.01) |

(52) U.S. Cl.
CPC .............. *C07C 17/395* (2013.01); *B01D 3/009* (2013.01); *B01D 3/10* (2013.01); *B01D 11/04* (2013.01); *B01J 19/123* (2013.01); *B01J 27/10* (2013.01); *C07C 17/25* (2013.01); *C07C 17/383* (2013.01); *C07C 21/18* (2013.01); *B01J 2219/1203* (2013.01)

(58) Field of Classification Search
CPC ...... C07C 17/395; C07C 19/08; C07C 17/38; C07C 17/00; C07C 17/357
USPC .................................................. 570/155, 177
See application file for complete search history.

(56) References Cited

U.S. PATENT DOCUMENTS

| | | | |
|---|---|---|---|
| 5,569,797 A * | 10/1996 | Fu et al. .......................... | 570/177 |
| 6,077,982 A * | 6/2000 | Yates et al. ..................... | 570/177 |
| 2007/0197842 A1 * | 8/2007 | Mukhopadhyay et al. ... | 570/155 |

* cited by examiner

*Primary Examiner* — Jafar Parsa
(74) *Attorney, Agent, or Firm* — Bruce Bradford

(57) ABSTRACT

The instant invention relates to a process and method for manufacturing 2,3,3,3-tetrafluoropropene by dehydrohalogenating a reactant stream of 2-chloro-1,1,1,2-tetrafluoropropane that is substantially free from impurities, particularly halogenated propanes, propenes, and propynes.

24 Claims, 3 Drawing Sheets

PROCESS FOR PRODUCING 2,3,3,3-TETRAFLUOROPROPENE

CROSS-REFERENCE TO RELATED APPLICATIONS

This application is a division of U.S. application Ser. No. 13/281,063, filed Oct. 25, 2011, now U.S. Pat. No. 8,975,454, issued Mar. 10, 2015, which application is related to and claims the priority benefit of U.S. provisional application No. 61/414,074 filed Nov. 16, 2010. The contents of each of the above noted application is which are incorporated herein by reference.

U.S. application Ser. No. 13/281,063 is also a continuation-in-part of U.S. application Ser. No. 12/510,740, filed Jul. 28, 2009, now U.S. Pat. No. 8,766,020, issued Jul. 1, 2014, which claims the priority benefit of U.S. provisional application No. 61/085,141, filed Jul. 31, 2008, the contents of each of which are incorporated herein by reference.

FIELD OF THE INVENTION

This invention relates to a novel method for preparing fluorinated organic compounds, more particularly to a method for preparing fluorinated olefins, and even more particularly to a method for producing 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

One known precursor used to prepare HFO-1234yf is 2-chloro-1,1,1,2-tetrafluoropropane (HCFC-244bb). Indeed, there are numerous gas phase reactions that are known for the production of HFO-1234yf by HCFC-244bb dehydrochlorination. U.S. Pub. No. U.S. 2007/0197842, for example, teaches the synthesis of HFO-1234yf through gas phase HCFC-244bb dehydrochlorination in the presence of a carbon- and/or metal-based catalyst (e.g. nickel or palladium based catalysts). U.S. Pub. No. U.S. 2009/0043136 also teaches the preparation of HFO-1234yf through gas phase HCFC-244bb dehydrochlorination in the presence of a catalyst selected from the group consisting of (i) one or more metal halides, (ii) one or more halogenated metal oxides, (iii) one or more zero-valent metals/metal alloys, or (iv) a combination of two or more of the foregoing.

While the foregoing reactions disclose processes having relatively high conversion levels, such reactions are not without disadvantages. As illustrated herein, known processes for the production of HCFC-244bb often produce only about a 90% yield. Thus, the remainder of the product stream includes undesirable by-products and raw materials. These by-products and raw materials are surprisingly shown herein to have a detrimental impact on the ability to produce high purity HFO-1234yf when used in connection with one or more of the applications mentioned above. As a result, they reduce product yields and increase associated costs.

Based on the foregoing, there is a continuing need for an improved process of preparing high purity HFO-1234yf from HCFC-244bb. The instant invention and the embodiments presented herein addresses at least this need.

SUMMARY OF INVENTION

The present invention relates, in part, to the surprising discovery that, during the dehydrochlorination of HCFC-244bb to form 2,3,3,3-tetrafluoropropene (HFO-1234yf), even a small amount of certain impurities in the reactor feed, particularly the HCFC-244bb feed stock, have a significant negative impact on (a) the ability to purify the final HFO-1234yf product; (b) the stability of the dehydrochlorination catalyst; and/or (c) the resulting reaction product stream. The instant invention provides methods of improving the production of high purity HFO-1234yf by substantially purifying the HCFC-244bb feed prior to dehydrohalogenation.

In one aspect, the instant invention relates to a process for making 2,3,3,3-tetrafluoropropene and preferably high purity 2,3,3,3-tetrafluoropropene by (a) providing a distillation inseparable feed stream of 2-chloro-1,1,1,2-tetrafluoropropane and at least one impurity in an amount greater than about 500 parts per million; (b) treating the feed stream until it is substantially free from the at least one impurity; and (c) dehydrohalogenating the 2-chloro-1,1,1,2-tetrafluoropropane containing feed stream to produce 2,3,3,3-tetrafluoropropene. In certain embodiments, the treated feed stream contains less than 5% total weight of impurities, less than 3% total weight of impurities, less than 1% total weight of impurities, or less than 0.5% total weight of impurities.

Reactant stream impurities may include any one or more compounds that inhibit the ability to produce high purity 1234yf in high yields, the stability of the dehydrochlorination catalyst or otherwise have a negative impact on the resulting product stream (containing toxic impurities). In one embodiment, such impurities include one or more compounds of formula I:

$$X_aC \equiv CY_b-CZ_3 \qquad (I)$$

wherein the bond between the first and second carbon atoms is denoted as being either a single, double or triple bond; a is 1, 2, or 3, and b is 0, 1, or 2, and each individual X, Y, and Z are independently Cl, I, Br, F, or H, subject to the proviso that Formula I does not include 2-chloro-1,1,1,2-tetrafluoropropane or 2,3,3,3-tetrafluoropropene.

In certain embodiments of formula I, the impurities may include one or more compounds selected from the group halogenated propanes, halogenated propenes, or halogenated propynes. Such impurities include, but are not limited to, one or a combination of 1,1,1,2,2-pentafluoropropane (HFC-245cb), 1,1,1,2-tetrafluoropropane (HFC-254eb), 1,1,1,3-tetrafluoropropane (HFC-254fb), 3,3,3-trifluoropropene (HFO-1243zf), 2,3-dichloro-3,3-difluoropropene (HCFO-1232xf), 2-chloro-3,3,3-trifluoropropene (HCFO-1233xf), 1-chloro-3,3,3-trifluoropropene (HCFO-1233zd), 1,2-dichloro-3,3,3-trifluoropropene (HCFO-1223xd), chlorotetrafluoropropenes (HCFO-1224 isomers), 1,2,3,3,3-pentafluoropropene (HFO-1225ye (cis and trans isomers)), 1,3,3,3-tetrafluoropropene (HFO-1234ze (cis and trans isomers)), and 3,3,3-trifluoropropyne.

Improved product purity and catalyst stability is obtained when such impurities are contained in the following amounts: from 0 to about 400 part per million (ppm) of 3,3,3-trifluoropropene (HFO-1243zf), from 0 to about 200 ppm of 2,3-dichloro-3,3-difluoropropene (HCFO-1232xf), from 0 to about 200 ppm of 2-chloro-3,3,3-trifluoropropene (HCFO-1233xf), from 0 to about 200 ppm 1-chloro-3,3,3-trifluoropropene (HCFO-1233zd), from 0 to about 200 ppm 1,2-dichloro-3,3,3-trifluoropropene (HCFO-1223xd), from 0 to about 200 ppm chlorotetrafluoropropenes (HCFO-1224 isomers), from 0 to about 200 ppm 1,2,3,3,3-pentafluoropropene (HFO-1225ye (cis and trans isomers)), from 0 to about 200 ppm 1,3,3,3-tetrafluoropropene (HFO-1234ze (cis and trans isomers)), from 0 to about 200 ppm 1,1,1,2,2-pentafluoropropane (HFC-245cb), from 0 to about 200 ppm 1,1,1,2-tetrafluoropropane (HFC-254eb), from 0 to about 200 ppm 1,1,1,3-tetrafluoropropane (HFC-254fb), and from 0 to about 200 ppm of 3,3,3-trifluoropropyne. The foregoing amounts, however, are not limiting to the instant invention.

Methods of ensuring that the 2-chloro-1,1,1,2-tetrafluoropropane containing feed stream is substantially free from impurities include, but are not limited to, subjecting the feed stream to one or a combination of a photochlorination reaction, a hydrogenation reaction, distillation or a liquid-liquid extraction.

Accordingly, and in certain embodiments, the instant invention relates to a method for removing the impurities from a 2-chloro-1,1,1,2-tetrafluoropropane raw feed stock by (a) optionally, subjecting said 2-chloro-1,1,1,2-tetrafluoropropane raw feed stock to a photochlorination process; and (b) purifying 2-chloro-1,1,1,2-tetrafluoropropane feed to produce a substantially pure 2-chloro-1,1,1,2-tetrafluoropropane feed. The photochlorination process may include, but is not limited to, reacting impurities with chlorine ($Cl_2$) in the presence of electromagnetic radiation, which may include ultraviolet light. While a multitude of reaction conditions may be used, in one embodiment, the reaction proceeds in a gas phase or a liquid phase and at a temperature of about 0° C. to about 50° C.

The step of purifying said raw feed stock may include any purification or separation technique known in the art for extracting 2-chloro-1,1,1,2-tetrafluoropropane from impurities contained within either the raw feed stock or the photochlorinated feed stock. In one embodiment, the purification method includes distillation. To this end, the raw feed stock is distilled using one or more distillation columns or packed towers. While distillation may occur at atmospheric pressure, super-atmospheric pressure or under vacuum, in certain embodiments it is conducted at a pressure of less than about 300 psig. It may also be conducted at a temperature from about –10° C. to about 90° C. Again, the instant invention is not so limiting and may include other purification methods such as a liquid-liquid extraction, which may be used alone or in combination with other extraction methods.

In further embodiments, the instant invention relates to a method for removing the impurities from a 2-chloro-1,1,1,2-tetrafluoropropane feed by (a) subjecting said 2-chloro-1,1,1,2-tetrafluoropropane feed to a hydrogenation process; and (b) purifying the 2-chloro-1,1,1,2-tetrafluoropropane feed to produce a substantially pure 2-chloro-1,1,1,2-tetrafluoropropane feed. The hydrogenation process includes, but is not limited to, reacting impurities with hydrogen ($H_2$) in the presence of one or more catalysts. Such catalysts may include one or a combination of Pt, Pd, and Ni, either un-supported or supported on an inert support. In the latter context, support substrates may include one or more of the following: activated carbon, alumina, different metal oxides, zeolites, alumosilicates, and molecular sieves. While a multitude of reaction conditions may be used, in one embodiment, the hydrogenation reaction is performed in a gas phase or a liquid phase and at a temperature from about 50° C. to about 400° C.

The step of purifying said raw feed stock may include any purification or separation technique known in the art for extracting 2-chloro-1,1,1,2-tetrafluoropropane from impurities contained within either the raw feed stock or the hydrogenated feed stock. In one embodiment, the purification method includes distillation. To this end, the raw feed stock is distilled using one or more distillation columns or packed towers. While distillation may occur at atmospheric pressure, super-atmospheric pressure or under vacuum, is conducted at a pressure of less than about 300 psig in certain embodiments. It may also be conducted at a temperature from about –10° C. to about 90° C. Again, the instant invention is not so limiting and may include other purification methods such as a liquid-liquid extraction, which may be used alone or in combination with other extraction methods.

In further embodiments, the instant invention relates to a process for producing high purity 2,3,3,3-tetrafluoropropene by (a) providing a feed stream comprising 2-chloro-1,1,1,2-tetrafluoropropane and at least one impurity; (b) subjecting the raw feed stock to either or both a photochlorination process and a hydrogenation process to form a modified feed stream; (c) purifying 2-chloro-1,1,1,2-tetrafluoropropane from the raw feed reaction stream or modified feed stream to produce a substantially pure 2-chloro-1,1,1,2-tetrafluoropropane feed stock; and (d) dehydrohalogenating said substantially pure 2-chloro-1,1,1,2-tetrafluoropropane feed stock. Non-limiting methods associated with each of the foregoing steps are provided herein.

Additional embodiments and advantages to the instant invention will be readily apparent to one of skill in the art based on the disclosure provided herein.

DETAILED DESCRIPTION OF THE INVENTION

Figure 1:
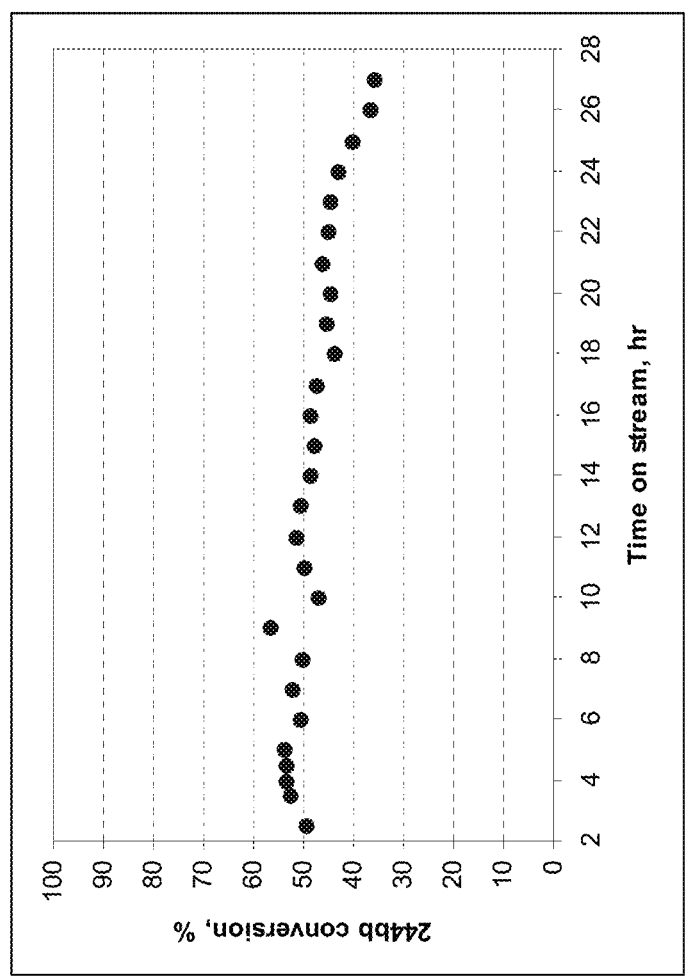
FIG. 1 illustrates the 244bb conversion over $MgF_2$ catalyst with 89.7%244bb/7.3%1233xf/3.0% others feed (450° C., 1 atm, 6 g-organic/h)

As provided herein, the instant invention relates to the surprising discovery that, during the dehydrochlorination of HCFC-244bb to form 2,3,3,3-tetrafluoropropene (HFO-1234yf), even a small amount of certain impurities in the reactor feed, particularly the HCFC-244bb feed stock, have a significant negative impact on (a) the ability to purify the final HFO-12334yf product; (b) the stability of the dehydrochlorination catalyst; and/or (c) the resulting reaction product stream. Accordingly, the instant invention, at least in part, relates the methods of improving the production of high purity HFO-1234yf by substantially purifying the HCFC-244bb reactor feed.

As used herein, the term "impurity," "impurities," or "unsaturated impurities" may include any chemical compound, particularly a halocarbon-based compound, within the HCFC-244bb stream that interferes with the stability of the dehydrochlorination catalyst or otherwise reduces the conversion rate and/or selectivity of HCFC-244bb to HFO- 1234yf. In particular embodiments, such impurities may be represented by the following formula I:

$$X_aC \equiv CY_b-CZ_3 \qquad (I)$$

wherein the bond between the first and second carbon atoms is denoted as being either a single, double or triple bond; a is either 1, 2, or 3, and b is either 0, 1, or 2, depending on the number of atoms necessary to satisfy the valence requirements of each respective carbon atom, and wherein each individual X, Y, and Z are independently Cl, I, Br, F, or H. The foregoing formula is subject to the proviso, however, that it does not include either HCFC-244bb or HFO-1234yf.

In another embodiment, the impurities of the instant invention and of formula I include, but are not limited to, halogenated propanes, halogenated propenes, or halogenated propynes and combinations thereof. Exemplified halogenated propane impurities include, but are not limited to, 1,1,1,2,2-pentafluoropropane (HFC-245cb), 1,1,1,2-tetrafluoropropane (HFC-254eb), 1,1,1,3-tetrafluoropropane (HFC-254fb), and combinations thereof. Exemplified halogenated propenes include, but are not limited to, 3,3,3-trifluoropropene (HFO-1243zf), 2,3-dichloro-3,3-difluoropropene (HCFO-1232xf), 2-chloro-3,3,3-trifluoropropene (HCFO-1233xf), 1-chloro-3,3,3-trifluoropropene (HCFO-1233zd), 1,2-dichloro-3,3,3-trifluoropropene (HCFO-1223xd), chlorotetrafluoropropenes (HCFO-1224 isomers), 1,2,3,3,3-pentafluoropropene (HFO-1225ye (cis and trans isomers)), 1,3,3,3-tetrafluoropropene (HFO-1234ze (cis and trans isomers)), and combinations thereof. An exemplified halogenated propyne includes, but is not limited to, 3,3,3-trifluoropropyne.

As provided herein, one aspect of the instant invention is removal of such impurities to form a substantially pure HCFC-244bb reaction stream or HCFC-244bb that is substantially free from impurities. As used herein the terms "substantially pure" or "substantially free" refer to the HCFC-244bb reactant stream having an amount of one or more impurities removed therefrom so as to improve the ability to produce high purity HFO-1234yf, improve yields, and decrease associated costs. In one aspect, the impurities are "substantially free" in that they do measurably impede the conversion of 244bb to 1234yf. In one embodiment, the final HCFC-244bb stream contains not more than about 5% total weight of the impurities. In further embodiments, it refers to the HCFC-244bb reactant stream having not more than 3% total weight of the impurities. In even further embodiments, it refers to the HCFC-244bb reactant stream having not more than 1% total weight of the impurities. In even further embodiments, it refers to the HCFC-244bb reactant stream having not more than 0.5% total weight of the impurities.

In even further embodiments, final 1234yf product purity and catalyst stability is obtained when such impurities in the final reactant feed stream are reduced to the following amounts: from 0 to about 400 part per million (ppm) of 3,3,3-trifluoropropene (HFO-1243zf), from 0 to about 200 ppm of 2,3-dichloro-3,3-difluoropropene (HCFO-1232xf), from 0 to about 200 ppm of 2-chloro-3,3,3-trifluoropropene (HCFO-1233xf), from 0 to about 200 ppm 1-chloro-3,3,3-trifluoropropene (HCFO-1233zd), from 0 to about 200 ppm 1,2-dichloro-3,3,3-trifluoropropene (HCFO-1223xd), from 0 to about 200 ppm chlorotetrafluoropropenes (HCFO-1224 isomers), from 0 to about 200 ppm 1,2,3,3,3-pentafluoropropene (HFO-1225ye (cis and trans isomers)), from 0 to about 200 ppm 1,3,3,3-tetrafluoropropene (HFO-1234ze (cis and trans isomers)), from 0 to about 200 ppm 1,1,1,2,2-pentafluoropropane (HFC-245cb), from 0 to about 200 ppm 1,1,1,2-tetrafluoropropane (HFC-254eb), from 0 to about 200 ppm 1,1,1,3-tetrafluoropropane (HFC-254fb), and from 0 to about 200 ppm of 3,3,3-trifluoropropyne.

The methods of removing the impurities from the HCFC-244bb reactant feed may include one or a combination of methods that are known in the art. In one embodiment, the methods include the following steps: (a) providing a raw feed stock comprising HCFC-244bb and one or more impurities; (b) subjecting said raw feed stock to a photochlorination process or hydrogenation process to produce a modified feed stock comprising a reduced amount of at least one of said impurities compared to said raw feedstock, preferably a reduced amount of the unsaturated halocarbon impurities compared to said raw feed stock; (c) purifying said raw feed stock or said modified feed stock to produce a substantially pure feed stock via an extraction or separation technique, wherein said high purity feed stock comprises relatively fewer impurities when compared to said raw feed stock or said modified feed stock; (d) subjecting said substantially pure feed stock to conditions effective to dehydrochlorinate at least a portion of said HCFC-244bb to produce a reaction product comprising relatively more HFO-1234yf, as compared to a reaction product using a feed that is not substantially free of impurities. To this end, the substantially pure reactant feed is effective to produce a final product comprising a majority of HFO-1234yf and a minority, if any, of impurities.

The initial step of producing HCFC-244bb may be accomplished using one or more methods that are known in the art. One such non-limiting method is the hydrofluorination of HCFO-1233xf, such as that disclosed in U.S. application Ser. No. 12/338,466, the contents of which are incorporated herein by reference. To this end, catalysts are employed to enhance the single-pass conversion of HCFO-1233xf to HCFC-244bb via HF addition across the double bond of HCFO-1233xf. Catalysts for performing this step may include, but are not limited to, $SbCl_3$, $SbCl_5$, $SbF_5$, $TiCl_4$, $SnCl_4$, $Cr_2O_3$, and fluorinated $Cr_2O_3$. The hydrofluorination process may be carried out in a vapor phase or a liquid phase.

In vapor-phase hydrofluorination, HF (hydrogen fluoride gas) is fed continuously through the catalyst bed. After a short time with only the HF feed stream, HCFO-1233xf is fed continuously through the catalyst bed at a ratio of about 1:1 to about 1:30 and preferably from about 1:2 to about 1:15 (HCFO-1233xf/HF mole ratio). The reaction between HF and HCFO-1233xf is carried out at a temperature from about 30° C. to about 400° C. (preferably from about 100° C. to about 300° C.) and at a pressure of about 5 psia to about 200 psia (pounds per square inch absolute) (preferably from about 30 psia to about 175 psia). The catalyst may be supported on a substrate, such as on activated carbon, or may be unsupported or free-standing. In addition to activated carbon, useful catalyst supports include: alumina, fluorinated alumina, aluminum fluoride, alkaline earth metal oxides, fluorinated alkaline earth metals, zinc oxide, zinc fluoride, tin oxide, and tin fluoride. The catalyst may (or may not) have to be activated with anhydrous hydrogen fluoride HF (hydrogen fluoride gas) before use depending on the state of the catalyst.

In liquid phase hydrofluorination, the catalyst is charged in a liquid form to a reactor and optionally activated with HF. The activated catalyst is then heated to the desired reaction temperature of about 30° C. to about 200° C. (preferably from about 50° C. to about 120° C.) and the pressure is kept between about 15 psia to about 200 psia (preferably from about 50 psia to about 175 psia). After a short time with only HF feed, a HCFO-1233xf feed stream is fed continuously through the catalyst at a ratio of about 1:1 to about 1:30 and preferably about 1:2 to about 1:15 (HCFO-1233xf/HF mole ratio). If necessary, the catalyst can be kept activated by the continuous or batch addition of $Cl_2$ or a similar oxidizing agent.

The hydrofluorination reaction is preferably carried out to attain a conversion of about 70% or, preferably, about 90% or more. Conversion is calculated by the number of moles of reactant (HCFO-1233xf) consumed divided by number of moles of reactant (HCFO-1233xf) fed to the reactor multiplied by 100. The selectivity for HCFC-244bb attained is preferably about 60% or more and most preferably about 80% or more. Selectivity is calculated by number of moles of product (HCFC-244bb) formed divided by number of moles of reactant consumed.

Hydrofluorination may be carried out in a corrosion-resistant reaction vessel. Examples of corrosion-resistant materials are Hastelloy, Nickel, Incoloy, Inconel, Monel and fluoropolymer linings. The vessel may have a fixed catalyst bed, or contain liquid catalyst. If desired, inert gases such as nitrogen or argon may be employed in the reactor during operation.

The foregoing hydrofluorination steps are not necessarily limiting to the instant invention, however, and may also include derivative or alternative methodologies that are otherwise known in the art.

Once HCFC-244bb is produced, but before it is fed into the dehydrohalogenation reactor, it is processed for the reduction of reaction impurities using one or a combination of the methods provided herein. In certain embodiments, and prior to entering the HCFC-244bb dehydrochlorination reactor, the unsaturated impurities of the HCFC-244bb reactant feed are first converted, via a photochlorination reaction, into corresponding saturated halogenated hydrocarbons having increased chlorine content. More specifically, in the photochlorination reaction chlorine ($Cl_2$) reacts with the unsaturated impurities in the presence of an electromagnetic source, such as an ultraviolet light source.

In one embodiment of the photochlorination process, electromagnetic radiation, e.g. UV light, from a suitable source is directed through a reactor wall to interact with the impurities contained therein. The source of light may be any one of a number of arc or filament lamps known in the art. Quartz or borosilicate glass such as Pyrex glass may be employed as transparent material to construct the portion of the reactor wall through which the light passes and enters the reactor. The photochlorination may be continuously carried out in the gas phase, in which starting materials are vaporized and contacted with chlorine vapor in a reaction zone. Although a wide range of chlorination reaction conditions are believed to be suitable, in certain preferred embodiments the reaction temperature is from about 0° C. to about 50° C. Alternatively or additionally, the chlorination may be carried out in the liquid phase by feeding chlorine to a reactor containing starting materials, with it generally being preferred to control the reaction temperature below the boiling points of the starting materials and products.

In alternative or additional embodiments, the unsaturated impurities are converted, prior to entering the HCFC-244bb dehydrochlorination reactor, into corresponding saturated halogenated hydrocarbons having increased hydrogen content, preferably via hydrogenation in which hydrogen ($H_2$) reacts with the unsaturated impurities in the presence of a catalyst. In one embodiment of the hydrogenation process, a suitable catalyst is used to facilitate the hydrogenation reaction. Non-limiting examples of hydrogenation catalysts are Pt, Pd, Ni or mixtures thereof un-supported or supported on inert support. The catalyst support may include, but is not limited to, activated carbon, alumina, different metal oxides, zeolites, alumosilicates or molecular sieves.

The hydrogenation reactor can be made of any material of construction known in the art such as steel, stainless steel, or metal alloys, etc. It is preferable that the reactor is equipped with temperature and pressure control. The hydrogenation reaction may be continuously carried out in the gas phase, in which starting materials are vaporized and contacted with hydrogen gas in a reaction zone. Although a wide range of hydrogenation reaction conditions are believed to be suitable, in certain preferred embodiments the reaction temperature is from about 50° C. to about 400° C. Alternatively or additionally, the hydrogenation may be carried out in the liquid phase by feeding hydrogen to a reactor containing starting materials, with it generally being preferred to control the reaction temperature below the boiling points of the starting materials and products.

The feed stream, whether or not it was subjected to the photochlorination and/or hydrogenation, is then treated with one or a combination of compound separation techniques, such as, but not limited to, distillation and/or extraction. Although it is contemplated that a wide range of separation conditions can be used in accordance with the present invention, in certain embodiments the HCFC-244bb raw materials are distilled by passing through one or multiple standard distillation columns and/or packed towers, or the like, which may be provided at atmospheric pressure, super-atmospheric pressure or a vacuum. Preferably, though not exclusively, the pressure is less than about 300 psig, more preferably less than about 150 psig and most preferably less than 100 psig.

The HCFC-244bb may be recovered as distillate by operating the distillation column at from about −10° C. to about 90° C., preferably from about 0° C. to about 80° C. While not limited thereto, multiple distillation columns may be preferred because of the presence of an azeotrope or azeotrope-like composition of HCFO-1233xf and HCFC-244bb that is known to exist.

In alternative or additional embodiments, the HCFC-244bb stream may be purified using extraction techniques that are known in the art. One such extraction technique is a liquid-liquid extraction, where HCFC-244bb is extracted based on its known solubility in one or more solvents.

Using one or a combination of the foregoing extraction or separation techniques, the HCFC-244bb reactant feed is substantially pure or substantially free from impurities, as defined herein. In certain not limiting embodiments, the resulting stream is at least about 99.5% pure HCFC-244bb with less than 5000 ppm of the impurities and the reactant feed is ready for transfer to the dehydrohalogenation reactor.

The dehydrochlorination step can be carried out using one or more known process techniques for conversion of HCFC-244bb to HFO-1234yf. To this end, catalytic conversion of HCFC-244bb is conducted under any conditions effective to dehydrochlorinate HCFC-244bb to produce HFO-1234yf. Preferably, though not exclusively, dehydrochlorination of HCFC-244bb is done in a vapor phase, such as a fixed-bed reactor in the vapor phase. The dehydrohalogenation reaction may be conducted in any suitable reaction vessel or reactor, but is preferably, though not exclusively, conducted in a reactor constructed from materials which are resistant to the corrosive effects of hydrogen chloride (to the extent that such material is formed under the dehydrohalogenation conditions). Exemplified materials for such a reactor include, but are not limited to, nickel and its alloys, including Hastelloy, Inconel, Incoloy, and Monel or vessels lined with fluoropolymers and may employ single or multiple tubes packed with a dehydrohalogenation catalyst.

The catalysts for the dehydrohalogenation reaction may include metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$ and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

The HCFC-244bb is introduced into the reactor either in pure form, partially purified form, or as part of the reactor effluent from the preceding step. The HCFC-244bb may optionally be fed with an inert gas diluent such as nitrogen, argon, or the like. In a preferred, though non-exclusive, embodiment of the invention, the HCFC-244bb is pre-vaporized or preheated prior to entering the reactor. Alternately, the HCFC-244bb is vaporized inside the reactor.

Useful reaction temperatures may range from about 100° C. to about 700° C. Preferred temperatures may range from about 150° C. to about 600° C., and more preferred temperatures may range from about 200° C. to about 550° C. The reaction may be conducted at atmospheric pressure, super-atmospheric pressure or under vacuum. The vacuum pressure can be from about 5 torr (0.0966 psia) to about 760 torr (14.69 psia). Contact time of the HCFC-244bb with the catalyst may range from about 0.5 seconds to about 120 seconds, however, longer or shorter times can be used.

In such dehydrochlorination embodiments, the conversion of the HCFC-244bb is at least about 10%, more preferably at least about 20%, and even more preferably at least about 30%. Preferably in such embodiments, the selectivity to HFO-1234yf, is at least about 70%, more preferably at least about 85% and more preferably at least about 95%.

In certain embodiments, the process flow is in the down or up direction through a bed of the catalyst. It may also be advantageous to periodically regenerate the catalyst after prolonged use while in place in the reactor. Regeneration of the catalyst may be accomplished by any means known in the art such as using an oxidizing agent such as $O_2$ or chlorine. For example, by passing air or air diluted with nitrogen over the catalyst at temperatures of from about 100° C. to about 400° C., preferably from about 200° C. to about 375° C., for from about 0.5 hour to about 3 days depending on the size of the reactor.

In general, the effluent from the dehydrohalogenation reaction step, including any intermediate effluents that may be present in multi-stage reactor arrangements, may be processed to achieve desired degrees of separation and/or other processing. For example, in embodiments in which the reactor effluent comprises HFO-1234yf, the effluent will generally also include HCl and unreacted HCFC-244bb. Some portion or substantially all of these components of the reaction product may be recovered from the reaction mixture via any separation or purification method known in the art such as neutralization and distillation. It is expected that unreacted HCFC-244bb could be recycled, completely or partially, to improve the overall yield of the desired $CF_3CF=CH_2$ (HFO-1234yf). Optionally but preferably, hydrogen chloride is then recovered from the result of the dehydrochlorination reaction. Recovering of hydrogen chloride is conducted by conventional distillation where it is removed from the distillate.

Alternatively, HCl can be recovered or removed by using water or caustic scrubbers. When a water extractor is used HCl is removed as an aqueous solution. When caustic is used, HCl is just removed from system as a chloride salt in aqueous solution.

The following are examples of the invention and are not to be construed as limiting.

EXAMPLES

Example 1

This example illustrates the continuous liquid phase fluorination reaction of 2-chloro-3,3,3-trifluoropropene (HCFO-1233xf)+HF→2-chloro-1,1,1,2-tetrafluoropropane (HCFC-244bb). The fluorination catalyst for the experiment was $SbCl_5$.

About 5618 grams of $SbCl_5$ were contained in a Teflon™-lined liquid phase reactor equipped with a 2-inch ID (inside diameter) packed column and a condenser. The reactor was 2.75-inch ID×36-inch L (length). Initially, a greater than 5:1 mole ratio of HF was added to the reactor to fluorinate the catalyst. A greater than 3:1 mole ratio of $Cl_2$ was then added to the reactor to ensure that the catalyst was brought back to a pentavalent state. The reactor was heated to about 85° C.-87° C. HF feed was started first. When an additional 1.5 lbs of HF had been added the 2-chloro-3,3,3-trifluoropropene feed was started. The purity of the 2-chloro-3,3,3-trifluoropropene feed stock was about 97.3 GC (gas chromatograph) area %. The experiment ran continuously for about 162 hours. For this run, chlorine was fed batchwise about every 4 hours throughout the run to keep the catalyst active.

Conversion was immediately above 98%, and remained that way throughout the rest of the run. The average feed rates of HF and HCFO-1233xf were 0.91 and 0.88 lb/hr respectively. The chlorine additions amounted to about 3.0% by weight of the average organic feed rate. About 123 pounds of acid-free 2-chloro-1,1,1,2-tetrafluoropropane crude were collected.

The reactor temperature range for the experiments was 78° C.-86° C. and the pressure range was 70 psig-105 psig. The reaction was monitored by sampling the reactor effluent stream periodically. The samples were analyzed on a gas chromatograph. The average conversion of 2-chloro-3,3,3-trifluoropropene (HCFO-1233xf) of about 98% and the following average product selectivity: HCFC-244bb=90%, HCFO-1223xd=1% and HFC-245cb=8%.

Example 2

This example illustrates the difficulty in obtaining high purity 244bb using a conventional batch distillation column The crude HCFC-244bb produced in a reaction run similar to that described in Example 1 was continuously fed into a caustic scrubber to remove unreacted HF and HCl by-product (formed during impurity formation). Then the product stream was passed through a column filled with desiccant to remove residual moisture and collected. 100 lbs of this material was charged to a distillation column consisting of a 10 gallon reboiler, 2 inch ID by 10 foot column packed with ¼" Propak packing, and a shell and tube heat exchanger for a condenser. The column had about 30 theoretical plates. The distillation column was equipped with temperature, pressure, and differential pressure transmitters. The distillation was run at 27 psig pressure and D/P in the range of 13-15 inches of H2O. The composition of the material charged to the distillation column was 3.85 GC area % HFC-245cb, 91.2 GC area % HCFC-244bb, 2.46 GC area % HCFO-1233xf, 1.1% GC area % HCFO-1223xd, and 1.4 GC area % including HCFO-1232xf, HFO-1243zf, chlorotetrachloropropene isomers, HCFO-1223zd, HFO-1234ze, HFO-1225ye, HFC-254eb, HFC-254fb, and 3,3,3-trifluoropropyne, among others. Only 40 lbs of 99.25 GC area % HCFC-244bb was recovered from the distillation. Impurities included 1233xf, chlorotetrafluoropropenes, 1233zd, 1223xd, and 1243zf. Additionally, 46 lbs of 94 GC area % HCFC-244bb and 5 GC area % HCFO-1233xf mixture was recovered and contained the same impurities as above with the addition of 245cb and 3,3,3-trifluoropropyne.

Example 3

The 99.25 GC area % HCFC-244bb recovered in Example 2 was used as feed to a reactor containing a dehydrochlorination catalyst. The reaction was highly selective to HFO-1234yf and a crude HFO-1234yf product that contained <1.0 GC area % impurities other than unconverted HCFC-244bb was produced. Using relatively pure HCFC-244bb as a feed to the dehydrochlorination reaction also improved dehydrochlorination catalyst stability. Catalyst stability was constant for over 1000 hours of continuous run time as compared to <500 hours using unpurified 244bb feed.

Example 4

A crude HCFC-244bb stream composed of 3.85 GC area % HFC-245cb, 91.2 GC area % HCFC-244bb, 2.46 GC area % HCFO-1233xf, 1.1% GC area % HCFO-1223xd, and 1.4 GC area % others including HCFO-1232xf, HFO-1243zf, chlorotetrachloropropene isomers, HCFO-1223zd, HFO-1234ze, HFO-1225ye, HFC-254eb, HFC-254fb, and 3,3,3-trifluoropropyne among others is charged into a jacketed photochlorination reactor where a 450 watt ultraviolet light source is present and turned on. A stream of $Cl_2$ is sparged into the photochlorination reactor where it adds across the double bonds of unsaturated impurities, especially 3,3,3-trifluoropropyne, HCFO-1233xf, HFO-1243zf and HCFO-1223xd producing high boiling products easily separated by conventional distillation. $Cl_2$ is added in a 20% excess to the stoichiometric amount needed to convert all the unsaturated compounds in the crude material. The reactor is run at near atmospheric pressure (0-10 psig) and the contents are cooled using circulating chilled brine through the reactor jacket. The reaction time is about 2 to about 4 hours. Regular sampling and subsequent GC analysis of the reactor contents confirms when the chlorination reaction is complete. A slightly caustic solution containing the amount of bisulfite required to neutralize unreacted chlorine in the reactor is added to a mixing tank. The amount of bisulfite used in the solution is about 0.015 weight percent and the amount of sodium hydroxide used in the solution is about 0.2%. The reaction mixture stream exits the photochlorination reactor and is added on top of the slightly caustic bisulfite solution in the mixing tank. The contents of mixing tank are well mixed by means of an agitator and any excess $Cl_2$ or hydrochloric acid (by-product of $Cl_2$ addition to saturated compounds) are neutralized by the bisulfite and caustic, respectively.

After mixing, the agitator is shut off and the contents of mixing tank are allowed to phase separate into an upper aqueous phase and a lower crude HCFC-244bb phase. The crude HCFC-244bb phase is then removed from the bottom of the mixing tank. After removal of the crude HCFC-244bb phase, the aqueous phase is removed for treatment. Then the acid and $Cl_2$ free crude HCFC-244bb stream enters a drying column where any residual or dissolved water is removed by a desiccant.

The dried crude HCFC-244bb exiting the drying column enters a conventional distillation column for separation of 2-chloro-1,1,1,2-tetrafluoropropane from impurities. Low boiling impurities such as HFC-245cb are removed first followed by a greater than 99.8 weight percent 2-chloro-1,1,1,2-tetrafluoropropane stream containing less than 500 ppm of unsaturated halogenated hydrocarbons.

Example 5

This example illustrates the continuous vapor phase hydrogenation reaction of crude HCFC-244bb to convert unsaturated impurities to saturated halocarbons that are easily separated from HCFC-244bb by any means known in the art such as distillation. Hydrogenation is performed using Monel reactor (ID 0.5 inches, length 32 inches) equipped with a vaporizer and preheater (ID 1 inch, length 32 inches) which is filled with Nickel mesh to enhance heat transfer. The reactor is filled with 50 milliliters of 1 wt % $Pd/Al_2O_3$ hydrogenation catalyst. Nickel mesh is placed at the top and at the bottom of reactor to support the catalyst. A multi-point thermocouple is inserted at the center of the reactor. A crude HCFC-244bb stream composed of 3.85 GC area % HFC-245cb, 91.2 GC area % HCFC-244bb, 2.46 GC area % HCFO-1233xf, 1.1% GC area % 1223xd, and 1.4 GC area % others including HCFO-1232xf, HFO-1243zf, chlorotetrachloropropene isomers, HCFO-1223zd, HFO-1234ze, HFO-1225ye, HFC-254eb, HFC-254fb, and 3,3,3-trifluoropropyne among others is vaporized and fed at the rate 1 lb/hr. Hydrogen is co-fed at a rate resulting in 20-80 mol % excess to the stoichiometric amount required to completely hydrogenate unsaturated impurities present in the crude HCFC-244bb feed. Hydrogen adds across the double bonds of unsaturated impurities, especially 3,3,3-trifluoropropyne, HCFO-1232xf, HCFO-1233xf, HFO-1243zf. HCFO-1223xd chlorotetrachloropropene isomers, HCFO-1223zd, HFO-1234ze and HFO-1225ye, producing both low- and high-boiling products that are easily separated from HCFC-244bb by conventional distillation. The reactor is heated to 200° C. by means of electric furnace. Reaction is run at the pressure about 45 psia.

The hydrogenated crude HCFC-244bb is charged to a conventional batch distillation column for separation of 2-chloro-1,1,1,2-tetrafluoropropane from impurities. Low boiling impurities such as HFC-245cb (−18° C.) and 263fb (BP −13° C.) are removed first followed by a greater than 99.8 weight percent 2-chloro-1,1,1,2-tetrafluoropropane distillate stream containing less than 500 ppm of unsaturated halogenated hydrocarbons.

Example 6

This example illustrates the negative effect of impurities in the 244bb feed material on the stability of a $MgF_2$ based dehydrohalogenation catalyst A cylindrical Monel reactor of ¾" diameter immersed into a 3-zone electrical furnace was used. Process temperatures were recorded using a multi-point thermocouple placed inside the reactor and within the catalyst bed. The distance between two adjacent probe points was 4". The catalyst was loaded in such a way that its bed was within two adjacent probe points. 244bb was fed into the bottom of the vertically mounted reactor and was vaporized before reaching catalyst bed. Effluent gases were passed through a gas sampling tube and the progress of the reaction was monitored periodically via GC analysis of the contents of the gas sampling tube. 20 ml of catalyst was charged and the flow rate of organic was 6 g/h in a typical run. As shown in FIG. 1, with 89.7%244bb/ 7.3%1233xf/3% others feed, 244bb conversion was decreased from above 50% initially to below 40% after only 24 hours on stream. The impurities in the feed caused premature deactivation of the dehydrochlorination catalyst.

Comparative Example 6

Figure 2:
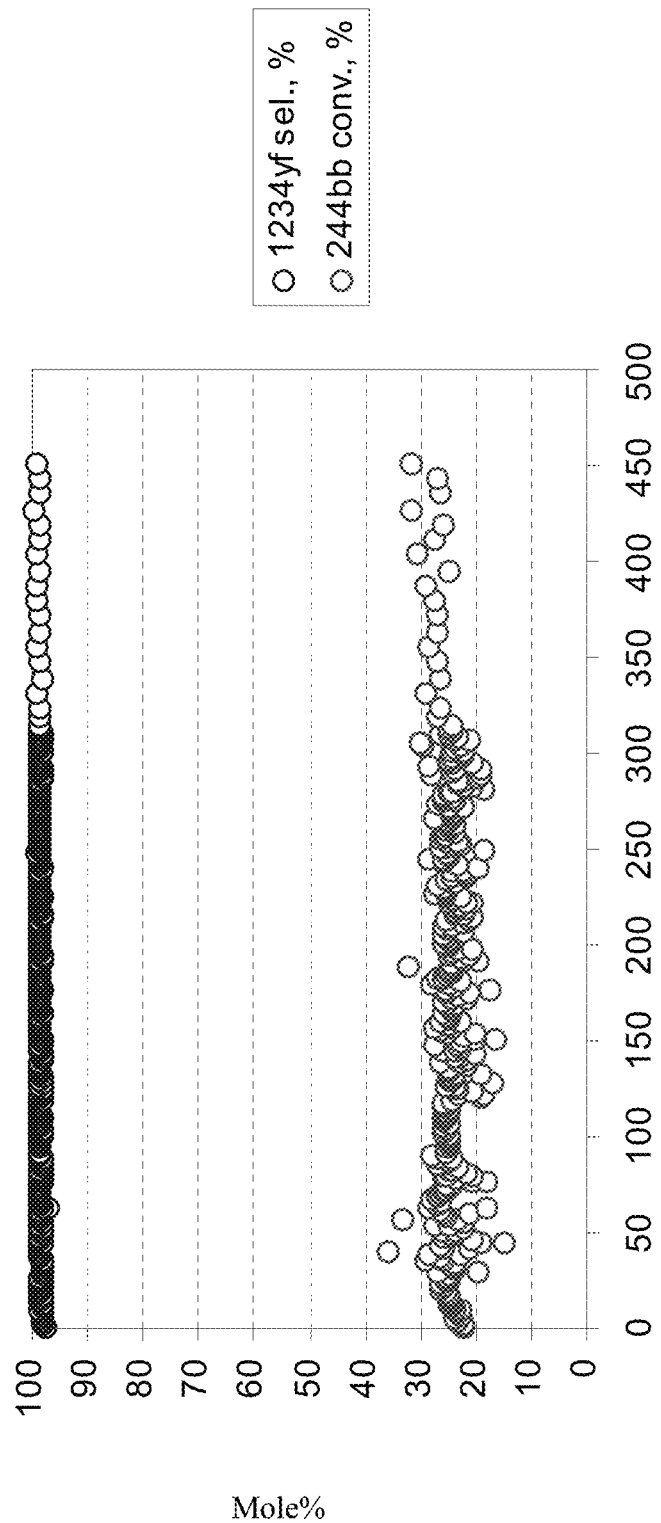
FIG. 2 illustrates the stability of 10 wt % CsCl/MgF2 Catalyst.

This comparative example shows that using a relatively pure 244bb feed material has a positive effect on the stability of a MgF$_2$ based dehydrohalogenation catalyst. The same set-up and reaction conditions that were used in Example 6 were used. The 244bb feed material was 99.0% pure with the major impurity being 1233xf at 0.8%. The catalyst FIG. 2 shows that the dehydrochlorination catalyst is stable for over 450 hours of on-stream time.

Example 7

This example illustrates the highly selective 244bb dehydrochlorination reaction to produce 1234yf in Inconel 625 reactor.

Figure 3:
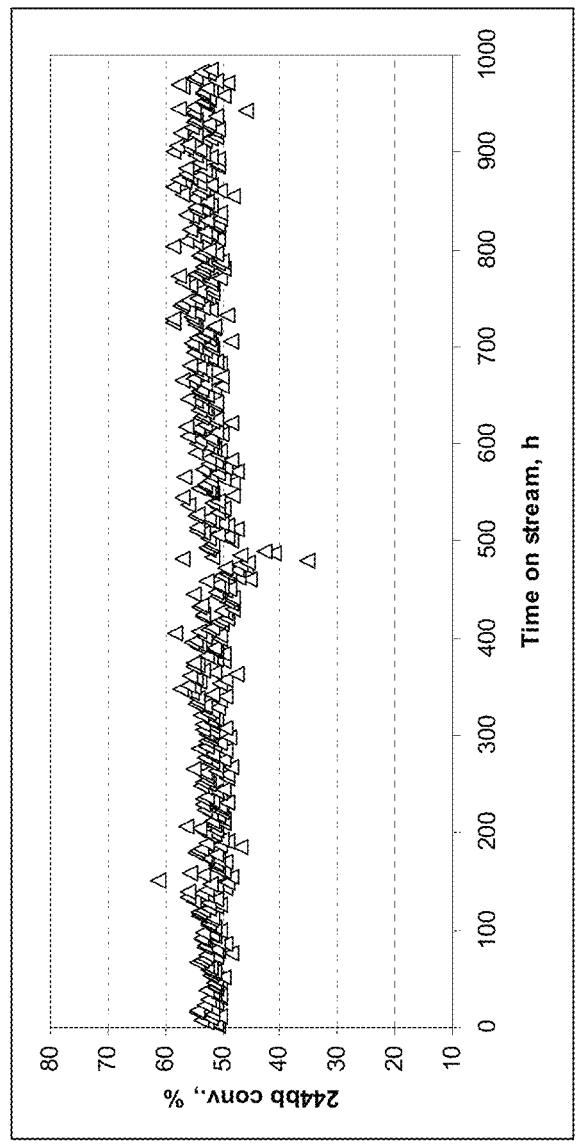
FIG. 3 illustrates 244bb conversion as a function of time on stream during 244bb dehydrochlorination in ¾" Inconel 625×0.035" reactor (480° C., ~25 psig)

A cylindrical Inconel 625 reactor of ¾" diameter immersed into a 3-zone electrical furnace was used. Process temperatures were recorded using a multi-point thermocouple placed inside the reactor. The 244bb feed material was of 99.37 GC area % purity and contained some unsaturated impurities with the major impurity being HCFO-1233xf at about 0.5 GC area % and about 0.13% other unsaturated compounds. The material had been purified by distillation only, which was not capable of removing certain unsaturated compounds. 244bb was fed into the bottom of the vertically mounted reactor and was vaporized before reaching reaction zone. Effluent gases were passed through a gas sampling tube and the progress of the reaction was monitored periodically via GC analysis of the contents of the gas sampling tube. As shown in FIG. 3, 244 bb conversions at 480° C. and 25 psig were generally between 50 and 55% (52.5% on average) and no deactivation was noted during the period of time of the test which lasted for about 1000 hours. The selectivity to 1234yf remained high at around 99.8% during the reaction.

A gas-bag sample was taken at 480° C. and 25 psig and analyzed by means of GC-MS. For comparison purpose, the feed was also analyzed. As shown in Table 1, other than trace amounts of C$_1$, C$_2$, and C$_4$ by-products, which were produced most likely through the breakage of 244bb and/or other molecules, no other by-products were formed during reaction. In addition, unsaturated species (such as 1233 and 1224) included in feedstock remained present in product stream, indicating no reaction occurred to those unsaturated species during 244bb dehydrochlorination in Inconel 625 reactor.

TABLE 1

GC-MS analysis of products formed from 244bb dehydrohalogenation in Inconel 625 reactor

| | Species identified | |
|---|---|---|
| Peak # | Raw material | Products formed at 480° C.[1] |
| 1 | | G23 |
| 2 | | 134a |
| 3 | | 1234yf |
| 4 | | HCl |
| 5 | | 347 |
| 6 | 244bb | 244bb |
| 7 | 142b | 142b |
| 8 | 1224 | 1224 |
| 9 | 1233xf | 1233xf |
| 10 | 1224 | 1224 |
| 11 | 1233zd | 1233zd |
| 12 | 1224 iso | 1224 iso |
| 13 | 142 | |
| 14 | G30 | |

[1]Other reaction conditions: ~25 psig, 12 g-organic/h, and 99.4 GC area % 244bb/0.4 GC area % 1233xf Example 8

This example illustrates the difficulty in obtaining high purity 1234yf using a continuous conventional distillation column and 1234yf crude material produced from a 244bb feedstock containing >8% impurities including 3.85 GC area % HFC-245cb, 2.46 GC area % HCFO-1233xf, 1.1% GC area % 1223xd, and 1.4 GC area % others including HCFO-1232xf, HFO-1243zf, chlorotetrachloropropene isomers, HCFO-1223zd, HFO-1234ze, HFO-1225ye, HFC-254eb, 254fb, and 3,3,3-trifluoropropyne, among others. The crude HFO-1234yf produced in was continuously fed into a caustic scrubber to remove HCl by-product. Then the product stream was passed through a column filled with desiccant to remove residual moisture. An oil-less compressor was used to feed crude product into the distillation column that was maintained at 30-45 psig pressure. The distillation column consisted of a 10 gallon reboiler, 2 inch ID by 10 foot column packed with ¼" Propak packing, and a shell and tube heat exchanger for a condenser. The column had about 30 theoretical plates. The distillation column was equipped with temperature, pressure, and differential pressure transmitters. Distillation was performed in a continuous mode and the take-off rate was equal to the rate of production of HFO-1234yf in the reactor. The purity of distilled HFO-1234yf was only 99.0 GC area %. GC analysis of the distillate showed the presence of both lower boiling and higher boiling impurities including 3,3,3-trifluoropropyne, HFO-1243zf, chlorotetrachloropropene isomers, HCFO-1223zd, HFO-1234ze, HFC-245cb, HCFO-1233xf, and HCFC-244bb. HCFO-1223xd and HCFO-1232xf were not detected. The bottoms of the distillation column were discharged and recycled into the dehydrochlorination reactor.

Example 9

The distillation overhead material collected from the continuous distillation in Example 7 needed to be further purified by batch distillation to meet an internal Honeywell 1234yf product specification. The same distillation equipment described in Example 7 was used, but run in batch mode. The batch distillation was done at 50 psig pressure and D/P in the range of 20-35 inches of H$_2$O meaning the separation required a huge reflux stream. The starting purity of HFO- 1234yf was about 99 GC %. Take off rate was 0.5 lb/hr for the light cut and 0.5-1.0 lb/hr for the main cut. In both cases the light cut was about 7 wt % of the initial amount of material charged into reboiler. 50 lb of material was charged into reboiler. Weight of light cut was 3.5 lb (light cut was collected until the purity of HFO-1234yf exceeded 99.9%). The weight of the main HFO-1234yf cut was 36.5 lb. The purity of HFO-1234yf in the main cut was greater than 99.96 GC %. Distillation was stopped due to low level in the reboiler. Table 2 is the GC analysis of the purified HFO-1234yf.

TABLE 2

Summary of GC results for the sample of HFO-1234yf produced from HCFC-244bb using CsCl/MgF2 catalyst and distilled twice.

| Compound | Concentration (wt %) |
|---|---|
| HFO-1234yf | 99.9671% |
| Hexafluorobutyne | 8 ppm |
| R-245cb | 4 ppm |
| R-134a | 68 ppm |
| 3,3,3-trifluoropropyne | <1 ppm |
| R-1243zf | 198 ppm |
| R-1234ze | 11 ppm |
| R-1113 | 3 ppm |
| R-12 | 13 ppm |
| R-1131 | 6 ppm |
| R-1122a | 3 ppm |
| R-1140 | 7 ppm |
| R-244bb | 3 ppm |
| R-1233xf | <1 ppm |
| Unknown | 3 ppm |

Total unsaturates (other than HFO-1234yf) - 237 ppm

What is claimed is:

1. A method for removing one or more impurities from a composition containing 2-chloro-1,1,1,2-tetrafluoropropane comprising:
    providing a 2-chloro-1,1,1,2-tetrafluoropropane feed comprising 2-chloro-1,1,1,2-tetrafluoropropane and at least one impurity, said at least one impurity including one or more compounds of formula I:

$$X_aC \equiv CY_b\text{—}CZ_3 \qquad (I)$$

wherein the bond between the first and second carbon atoms is a triple bond; a is 1, and b is 0, and each individual X, Y, and Z are independently Cl, I, Br, F, or H, subject to the proviso that Formula I does not include 2-chloro-1,1,1,2-tetrafluoropropane or 2,3,3,3-tetrafluoropropene;
    subjecting said composition to photochlorination; and
    obtaining substantially pure 2-chloro-1,1,1,2-tetrafluoropropane.

2. The method of claim 1 wherein said photochlorination comprises reacting the impurities with chlorine (Cl$_2$) in the presence of electromagnetic radiation.

3. The method of claim 2 wherein the electromagnetic radiation is in the ultraviolet light spectrum.

4. The method of claim 1 wherein the photochlorination is carried out in the gas phase or the liquid phase.

5. The method of claim 1 wherein at least a portion of the photochlorination is carried out at a temperature of about 0° C. to about 50° C.

6. The method of claim 1 wherein the obtaining step comprises extraction.

7. The method of claim 6 wherein said extraction comprises distillation using one or more distillation columns.

8. The method of claim 7 wherein at least a portion of the distillation is performed at a pressure selected from the group consisting of atmospheric pressure, super-atmospheric pressure and under vacuum.

9. The method of claim 8 wherein the pressure is less than about 300 psig.

10. The method of claim 7 wherein at least a portion of the distillation is conducted at a temperature from about −10° C. to about 90° C.

11. The method of claim 6 wherein the extraction comprises liquid-liquid extraction.

12. A method for removing one or more impurities from a 2-chloro-1,1,1,2-tetrafluoropropane feed comprising:
    providing a 2-chloro-1,1,1,2-tetrafluoropropane feed comprising 2-chloro-1,1,1,2-tetrafluoropropane and at least one impurity, said at least one impurity including one or more compounds of formula I:

$$X_aC \equiv CY_b\text{—}CZ_3 \qquad (I)$$

wherein the bond between the first and second carbon atoms is a triple bond; a is 1, and b is 0, and each individual X, Y, and Z are independently Cl, I, Br, F, or H, subject to the proviso that Formula I does not include 2-chloro-1,1,1,2-tetrafluoropropane or 2,3,3,3-tetrafluoropropene;
    subjecting said 2-chloro-1,1,1,2-tetrafluoropropane feed to a purification process comprising hydrogenation process to produce a substantially pure 2-chloro-1,1,1,2-tetrafluoropropane feed.

13. The method of claim 12 wherein the hydrogenation comprises reacting the impurities with hydrogen (H$_2$) in the presence of one or more catalysts.

14. The method of claim 13 wherein the catalyst is selected from the group consisting of Pt, Pd, Ni, and mixtures thereof and is either un-supported or supported on inert support.

15. The method of claim 14 wherein the support is selected from the group consisting of activated carbon, alumina, different metal oxides, zeolites, alumosilicates, and molecular sieves.

16. The method of claim 12 wherein the hydrogenation is performed in a gas phase or a liquid phase.

17. The method of claim 12 wherein at least a portion of the hydrogenation is performed at a temperature from about 50° C. to about 400° C.

18. The method of claim 12 wherein the purification process comprises extraction.

19. The method of claim 18 wherein the extraction comprises distillation said using one or more distillation columns.

20. The method of claim 19 wherein at least a portion of the distillation is performed at a pressure selected from the group consisting of atmospheric pressure, super-atmospheric pressure and under vacuum.

21. The method of claim 20 wherein the pressure is less than about 300 psig.

22. The method of claim 19 wherein the distillation is conducted at a temperature from about −10° C. to about 90° C.

23. The method of claim 18 wherein the extraction comprises liquid-liquid extraction.

24. A process for producing substantially pure 2,3,3,3-tetrafluoropropene, comprising:
    providing a feed stream comprising 2-chloro-1,1,1,2-tetrafluoropropane and at least one impurity, said at least one impurity including one or more compounds of formula I:

$$X_aC \equiv CY_b\text{—}CZ_3 \qquad (I)$$

wherein the bond between the first and second carbon atoms is a triple bond; a is 1, and b is 0, and each individual X, Y, and Z are independently Cl, I, Br, F, or H, subject to the proviso that Formula I does not include 2-chloro-1,1,1,2-tetrafluoropropane or 2,3,3,3-tetrafluoropropene;

subjecting said 2-chloro-1,1,1,2-tetrafluoropropane feed stream to either or both a photochlorination process and a hydrogenation process to form a modified feed stream;
purifying 2-chloro-1,1,1,2-tetrafluoropropane from the modified feed stream to produce a substantially pure 2-chloro-1,1,1,2-tetrafluoropropane feed stream; and
dehydrohalogenating said substantially pure 2-chloro-1,1,1,2-tetrafluoropropane feed stock.

* * * * *